US00PP22903P2

(12) United States Plant Patent
Kivistik

(10) Patent No.: US PP22,903 P2
(45) Date of Patent: Jul. 31, 2012

(54) *CLEMATIS* PLANT NAMED 'UNAI 001'

(50) Latin Name: *Clematis jackmanii*
Varietal Denomination: UNAI 001

(76) Inventor: Aili Kivistik, Kose Parish (EE)

( * ) Notice: Subject to any disclaimer, the term of this patent is extended or adjusted under 35 U.S.C. 154(b) by 0 days.

(21) Appl. No.: 12/927,327

(22) Filed: Nov. 12, 2010

(51) Int. Cl.
*A01H 5/00* (2006.01)

(52) U.S. Cl. ..... Plt./228
(58) Field of Classification Search ..... Plt./228
See application file for complete search history.

*Primary Examiner* — Susan McCormick Ewoldt
(74) *Attorney, Agent, or Firm* — Cassandra Bright

(57) ABSTRACT

A new and distinct *Clematis* cultivar named 'UNAI 001' is disclosed, characterized by good resistance to normal diseases and pests of *Clematis*, continuous flowering from May through September, with flower buds continuously produced from the leaf axils. Plants are exceptionally floriferous and produce tepals colored Violet to Violet-Purple. The new cultivar is a *Clematis*, suitable for ornamental garden purposes.

2 Drawing Sheets

Latin name of the genus and species: *Clematis jackmanii.* Variety denomination: 'UNAI 001'.

BACKGROUND OF THE INVENTION

The new cultivar is a product of a planned breeding program conducted by the inventor that began in 1978. In 1982 the inventor, Aili Kivistik a citizen of Estonia, organized a group of unnamed, unpatented *Clematis jackmanii* varieties for an open pollination breeding project. Seeds originating from this open pollination were planted out, and the new variety was selected in 1985. Specific parents of the new variety are unknown, as the seed was bulk collected, without noting the variety collected from. All work was conducted at a non-commercial nursery in Roogoja, Estonia.

In 1989 the inventor first propagated 'UNAI 001' by vegetative cuttings at the same non-commercial nursery in Roogoja, Estonia. Subsequent generations have shown that the unique features of this cultivar are stable and reproduced true to type.

SUMMARY OF THE INVENTION

The cultivar 'UNAI 001' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'UNAI 001' These characteristics in combination distinguish 'UNAI 001' as a new and distinct *Clematis* cultivar:

1. Good resistance to diseases and pests common to *Clematis.*
2. Continuous flowering from May through September.
3. Very floriferous plants.
4. Flower buds produced continuously from the leaf axils.
5. Purple-Violet to Purple tepal coloration.

COMPARISON TO KNOWN VARIETIES

Plants of the new cultivar 'UNAI 001' are similar to known forms of *Clematis jackmanii* in most horticultural characteristics, however, plants of the new cultivar 'UNAI 001' produce flowers with larger, and more tepals than common forms of *Clematis jackmanii* known to the inventor. Additionally, plants of 'UNAI 001' flower continuously from May through September, whereas many known forms of *Clematis jackmanii* flower reliably 2 months only.

The new cultivar 'UNAI 001' can also be compared to the known variety *Clematis jackmanii* 'Superba'. Plants are similar in most horticultural characteristics, however, plants of the new cultivar produces flowers with 6 to 8 tepals, compared to 4 tepals on *Clematis* 'Superba'. Additionally the new cultivar begins blooming one month earlier.

The new cultivar 'UNAI 001' can also be compared to the known variety *Clematis jackmanii* 'Tie Dye' U.S. Plant Pat. No. 18,913. Plants are similar in most horticultural characteristics, however, plants of the new cultivar produces flowers that are larger, with more tepals. Additionally the new cultivar begins blooming one month earlier, and flowers one month later than 'Tie Dye'.

BRIEF DESCRIPTION OF THE PHOTOGRAPHS

Figure 1:
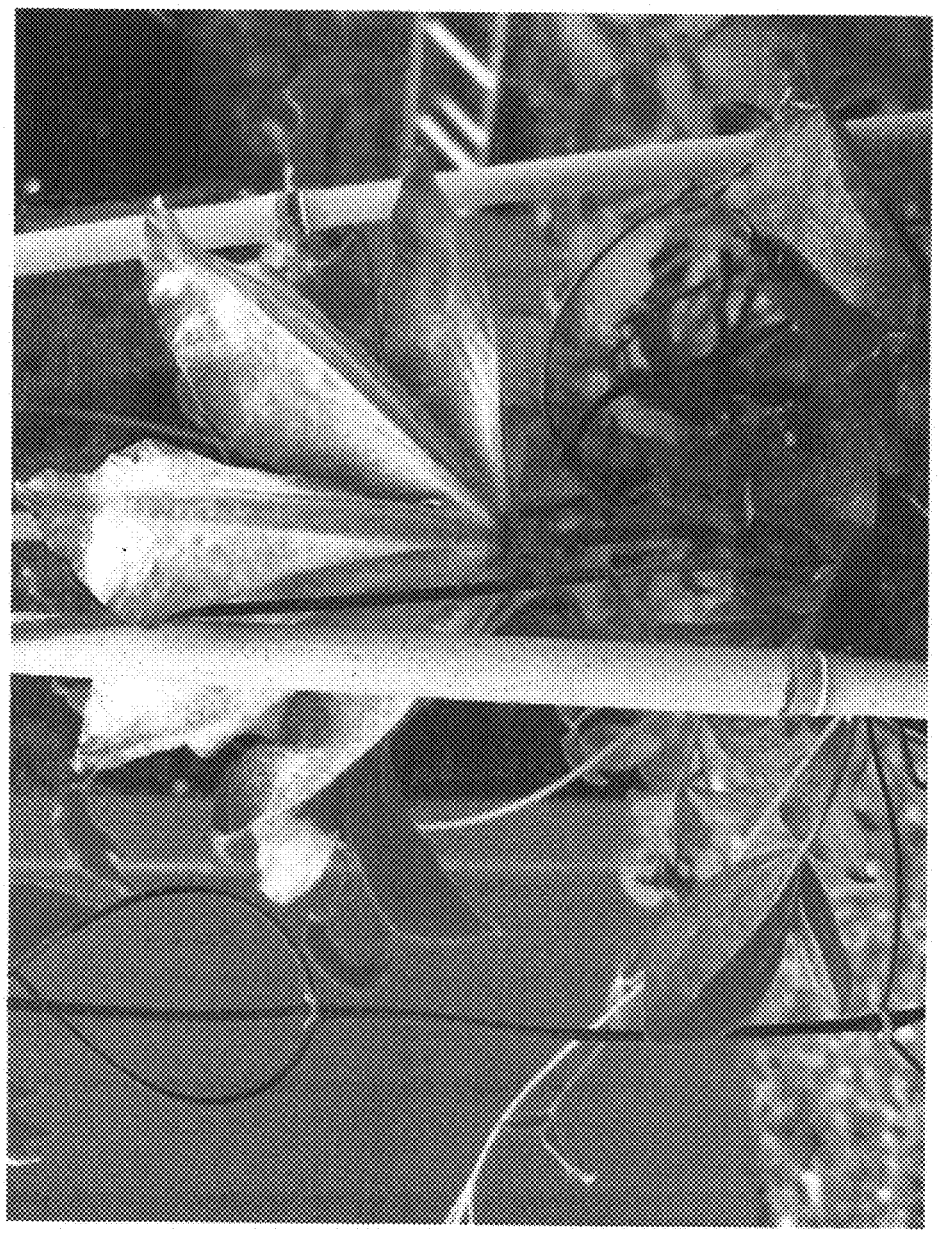

The accompanying photograph in FIG. 1 illustrates in full color a close up of typical foliage and the reverse side of flowers of 'UNAI 001'.

Figure 2:
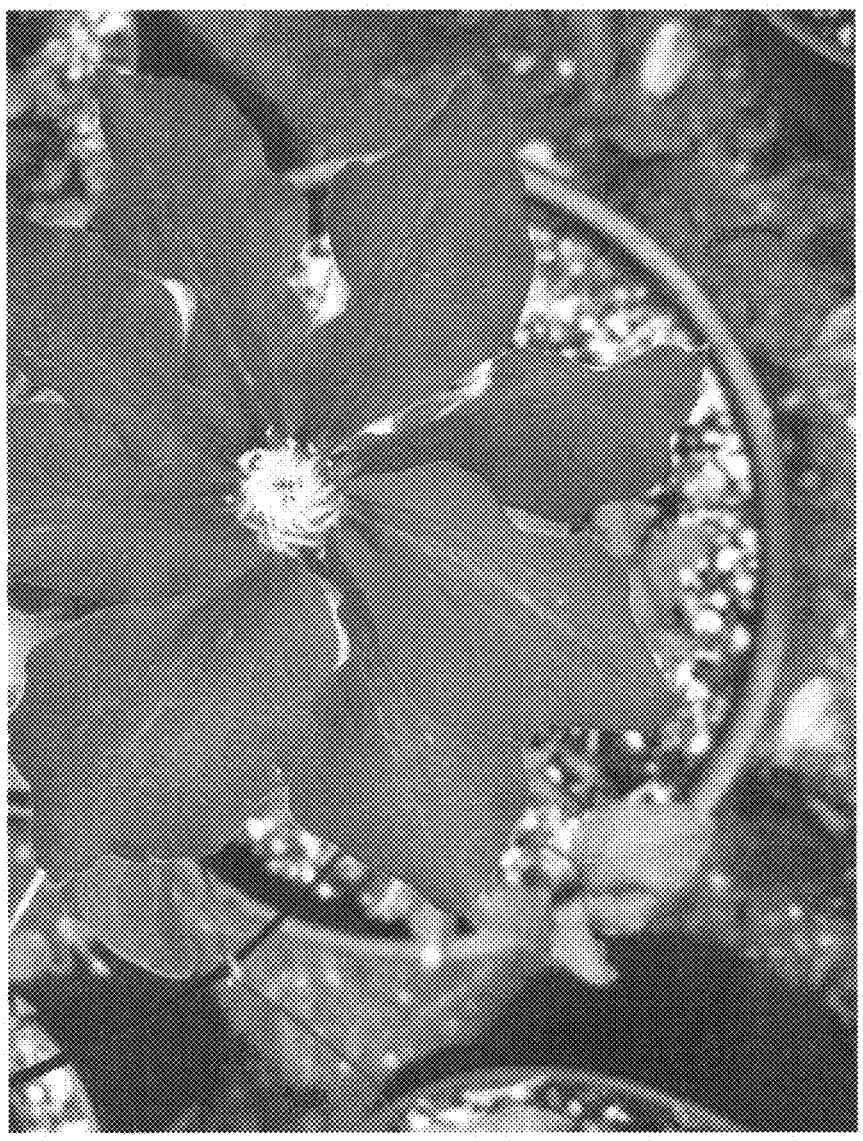

FIG. 2 shows a close up of a typical flower of 'UNAI 001' grown outdoors in Estonia.

The plant is less than one year old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'UNAI 001' plants grown outdoors in Roogoja, Estonia. Plants are approximately 1 year old, in a 1 liter nursery container. The growing conditions are outdoors and unshaded. Temperatures ranged from approximately −2° C. to 20° C. at night to 5° C. to 35° C. during the day. Measurements and numerical values represent averages of typical plant types.

Botanical classification: *Clematis jackmanii* 'UNAI 001'.

PROPAGATION

Time to rooting:

*Initiation*.—Approximately 40 days in the Summer at approximately 25° C.

*Rooted cuttings production*.—Approximately 40 days in the Summer at approximately 25° C.

Root description: Fine, fibrous.

PLANT

Growth habit: Climbing vine.

Height: Approximately 160 to 180 cm, measured from the soil line of the pot after approximately 1 year.

Plant spread: Approximately 80 cm when trained as a vine. Left untrained, approximately 150 cm.

Growth rate: Rapid. During active growing season in Spring, approximately 70 cm per month.

Branching characteristics: Very well branched, one main branch with at least 10 lateral branches.

Length of main stem: Approximately 160 to 180 cm.

Diameter of main stem: Approximately 0.2 to 0.5 cm.

Main stem color: Near RHS Brown 200B.

Main stem texture: Glabrous.

Internode length: Varies from 10 to 15 cm.

Strength: Strong, flexible, semi-woody.

FOLIAGE

Leaf:

*Type*.—Ternate leaves arranged opposite.

*Description ternate leaves*.—Leaves per lateral Branch: Approximately 48 leaflets. Average Length: Approximately 12 cm. Average Width: Approximately 8 cm. Leaflet Petiole: Average Length: Approximately 1.0 cm. Color: Near RHS Green 136A. Diameter: Approximately 0.2 cm. Texture: Glabrous.

*Leaflets*.—Average Length: Approximately 5 cm. Average Width: Approximately 3 cm. Shape of blade: Heart shaped. Apex: Acute. Base: Cordate. Attachment: Petioled. Margin: Entire. Texture of top surface: Smooth. Texture of bottom surface: Smooth. Leaf internode length: Approximately 2 cm. Resistance to stress and breakage: Very resistant to environmental and mechanical stress. Color: Young foliage upper side: Near RHS Green 136C. Young foliage under side: Near RHS Green 137D. Mature foliage upper side: Near RHS Green 136A. Mature foliage under side: Near RHS Green 137C. Venation: Type: Pinnate. Venation color upper side: Near RHS Green 136A. Venation color under side: Near RHS Green 137C. Petiole: Average Length: Approximately 5 cm. Color: Near RHS Green 136A. Diameter: Approximately 0.2 cm. Texture: Glabrous.

Tendrils not present.

FLOWER

Bloom period:

*Natural season*.—Continuously from approximately May through September.

Flower type and habit: Solitary axillary; flowers facing outward.

Flower longevity on plant: Approximately 5 days, after fully opened. Self-cleaning.

Quantity of flowers: Very free, continuous flowering. Mature plants have at least 50 open flowers during the flowering season.

Inflorescence size:

*Diameter*.—Approximately 14 cm.

*Depth*.—Approximately 1 cm.

Corolla:

*Tepal arrangement*.—Single to double whorl. Overlapping.

*Quantity*.—Approximately 6 to 8 per flower.

*Size*.—Length: Approximately 7 cm. Width: Approximately 5 cm.

*Margin*.—Entire.

*Apex*.—Acute.

*Base*.—Truncate.

*Aspect*.—Moderately concave. Margins slightly undulating.

*Texture*.—Smooth, velvety.

Color:

*Tepals*.—When opening: Upper surface: Near RHS Purple 75A with central bar near 78A. Lower surface: Near RHS Purple-Violet 82C with central bar near Red-Purple 70C. Fully opened: Upper surface: Near RHS Purple N78A, strong tinge Purple-Violet N81A. Lower surface: Near RHS Purple-Violet 82B and N82D.

*Ageing*.—Upper Surface: Near RHS Purple-Violet N81A. Lower surface: Near RHS Purple-Violet 82B and N82D.

Bud:

*Shape*.—Ovate.

*Length*.—Approximately 2 cm.

*Diameter*.—Approximately 1 cm.

*Color*.—Mainly Near RHS Green 138C.

Peduncles: Length: Approximately 6 cm. Width: Approximately 0.3 cm. Angle: Average 15°. Strength: Moderate. Color: Near RHS Green 138A.

*Fragrance*.—None.

REPRODUCTIVE ORGANS

Stamens:

*Number*.—Approximately 60 per flower.

*Anther length*.—0.6 cm.

*Anther color*.—Near RHS Yellow-Green 149D, 149C towards base.

*Anther shape*.—Oblong.

*Pollen quantity*.—Moderate.

*Pollen color*.—Near RHS Yellow 2C.

*Filament length*.—Approximately 0.6 cm.

*Filament aspect*.—Straight to slightly outwardly curved.

*Filament color*.—Near RHS Yellow 1 C.

Pistil:

*Number*.—Approximately 30 per flower.

*Length*.—Approximately 1.2 to 1.4 cm.

*Style color*.—Near RHS White 155B.

*Style length*.—Approximately 0.5 cm.
*Stigma*.—Shape: Linear. Color: Near RHS Yellow 11D.

OTHER CHARACTERISTICS

Seeds: Per flower, typically 30 round seeds, approximately 0.15 diameter. Colored near RHS Green 137B.

Disease/pest resistance: Very good resistance to pathogens and pests common to *Clematis* have been observed.

Temperature tolerance: Observed to tolerate temperatures from approximately −5° C. to at least 35° C.

What is claimed is:

1. A new and distinct cultivar of *Clematis* plant named 'UNAI 001' as herein illustrated and described.

* * * * *